United States Patent
Chen et al.

(10) Patent No.: US 10,105,400 B2
(45) Date of Patent: Oct. 23, 2018

(54) COMPOSITION OF CHICKEN LIVER HYDROLYSATES AND METHOD FOR IMPROVING ALCOHOL METABOLISM, AS WELL AS PREVENTING AND TREATING LIVER FIBROSIS

(71) Applicant: NATIONAL TAIWAN UNIVERSITY, Taipei (TW)

(72) Inventors: Yi-Chen Chen, Taipei (TW); Po-Ju Chen, Taipei (TW); Szu-Yun Tai, Taipei (TW)

(73) Assignee: National Taiwan University, Taipei (TW)

( * ) Notice: Subject to any disclaimer, the term of this patent is extended or adjusted under 35 U.S.C. 154(b) by 0 days.

(21) Appl. No.: 15/660,010

(22) Filed: Jul. 26, 2017

(65) Prior Publication Data
US 2018/0117095 A1    May 3, 2018

(30) Foreign Application Priority Data
Oct. 27, 2016    (TW) .............................. 105134821 A

(51) Int. Cl.
A61K 35/57    (2015.01)
A61K 31/198   (2006.01)
A61K 31/185   (2006.01)
A61K 31/4172  (2006.01)

(52) U.S. Cl.
CPC ............. *A61K 35/57* (2013.01); *A61K 31/185* (2013.01); *A61K 31/198* (2013.01); *A61K 31/4172* (2013.01)

(58) Field of Classification Search
None
See application file for complete search history.

(56) References Cited

U.S. PATENT DOCUMENTS

2014/0079818 A1    3/2014    Lee et al.

FOREIGN PATENT DOCUMENTS

TW    I411432 B    10/2013

OTHER PUBLICATIONS

Yang, et al., Food Chem., 160:148. (Year: 2014).*
Chen, et al., J. Agric. Food Chem., 65:4961. (Year: 2017).*

* cited by examiner

*Primary Examiner* — Michael Barker
(74) *Attorney, Agent, or Firm* — Rosenberg, Klein & Lee

(57) ABSTRACT

The invention relates to a composition of chicken liver hydrolysates and a method for improving alcohol metabolism, preventing and reducing liver alcoholic fatty liver and fibrosis. The chicken liver hydrolysates are prepared by a specific enzyme and comprise free amino acids such as leucine, lysine, alanine and glutamic acid.

9 Claims, 13 Drawing Sheets
(3 of 13 Drawing Sheet(s) Filed in Color)

CON

EtOH

CLH-L

CLH-M

CLH-H

SLM

CON

TAA

CLH-L

CLH-H

CNS

COMPOSITION OF CHICKEN LIVER HYDROLYSATES AND METHOD FOR IMPROVING ALCOHOL METABOLISM, AS WELL AS PREVENTING AND TREATING LIVER FIBROSIS

BACKGROUND OF THE INVENTION

Field of the Invention

The present invention relates to a composition of a chicken liver hydrolysates and a method for improving alcohol metabolism, as well as preventing and treating liver fibrosis. The chicken liver hydrolysates obtained from a specific manufacturing method can effectively improve alcohol metabolism and reduce collagen deposition in livers, so as to prevent liver fibrosis and alcohol-induced liver damage.

Description of Related Art

Liver diseases are severely healthy issues in Taiwan. Chronic liver diseases, liver cirrhosis and hepatitis have been listed in the 10 leading causes of death in Taiwan for a long time. Liver is a very important organ which performs multiple physiological functions, e.g. glycogen storage, plasma protein synthesis, lipid metabolism, detoxification, and so on. Thus, the liver damage results in extensive effects on human health. Liver damage may be caused by a chronic inflammation induced by virus infection, and alcohol or drug abuse. Chronic and persistent liver inflammation leading to a repeated tissue damage and repair may result in liver fibrosis and cirrhosis.

So far, there is no effective treatment for liver fibrosis or cirrhosis. Even the extensively used compound for liver protection in the western societies, silymarin, still cannot improve liver function significantly in clinical trials. Thus the development of liver-protective medicines has been always an important research topic. For example, the U.S. Pub. No. US 20140079818 A1, published on 20 Mar. 2014, disclosed a method for improving liver function in carbon tetrachloride (CCL4)-treated animals by applying a boehmeria extract; the Taiwan Patent No. I411432 B, issued on 11 Oct. 2013, disclosed that mangostin, a compound isolated from *Garcinia Mangostana* L, improved liver function in CCL4-treated or thioacetamide (TAA)-treated animals. However, there are still undesired situations to be noted when using plant extracts in liver protection, e.g. a high-dose of plant extract triggering cell toxicity, a long-term use of plant extracts leading to unwanted side effects and so on. Thus, it is quite necessary to develop a safer pharmaceutical composition for liver protection.

Liver damage induced by an excessive drinking is another important healthy issue. Some people cannot metabolize alcohol efficiently due to their genetic background and are prone to have alcohol-induced liver damage. Thus, how to prevent an alcohol-induced liver damage is also an important topic.

SUMMARY OF THE INVENTION

The present invention relates to a composition of chicken liver hydrolysates and a method for improving alcohol metabolism, preventing and treating liver fibrosis. The chicken liver hydrolysates comprise from 100 to 200 mg/g of free amino acids, and the free amino acids further comprise from 10 to 20 mg/g of leucine, from 10 to 20 mg/g of lysine, from 10 to 20 mg/g of alanine, and from 15 to 25 mg/g of glutamic acid.

In one aspect, the chicken liver hydrolysates comprise 11.28 mg/g of leucine, 10.68 mg/g of lysine, 10.01 mg/g of alanine, and 18.38 mg/g of glutamic acid.

In one aspect, the chicken liver hydrolysates further comprise at least one of taurine, carnosine, and anserine. Preferentially, the composition of the chicken liver hydrolysates comprises 20 to 60 mg/100 g taurine, 10 to 20 mg/100 g carnosine, and 150 to 250 mg/100 g anserine.

In one aspect, the composition of the chicken liver hydrolysates increases the activity of alcohol dehydrogenase and aldehyde dehydrogenase.

In one aspect, the composition of the chicken liver hydrolysates decreases serum and liver triglyceride.

In one aspect, the composition of the chicken liver hydrolysates decreases collagen deposition and the gene expression of collagen type 1α (Col1α) and α-smooth muscle actin (α-SMA) in livers.

In one aspect, the composition of the chicken liver hydrolysates decreases the gene expressions of tumor necrosis factor-α (TNF-α), interleukin-6 (IL-6), and transforming growth factor-β (TGF-β).

In one aspect, the composition of the chicken liver hydrolysates is orally administered to the individual in need thereof.

In one aspect, the composition of the chicken liver hydrolysates is made as pills, capsules, tablets, granules, powders, oral solution or suspension.

Therefore, the chicken liver hydrolysates prepared by a specific method provide liver-protective effect by decreasing collagen deposition in livers.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE PREFERRED EMBODIMENT

Figure 1:
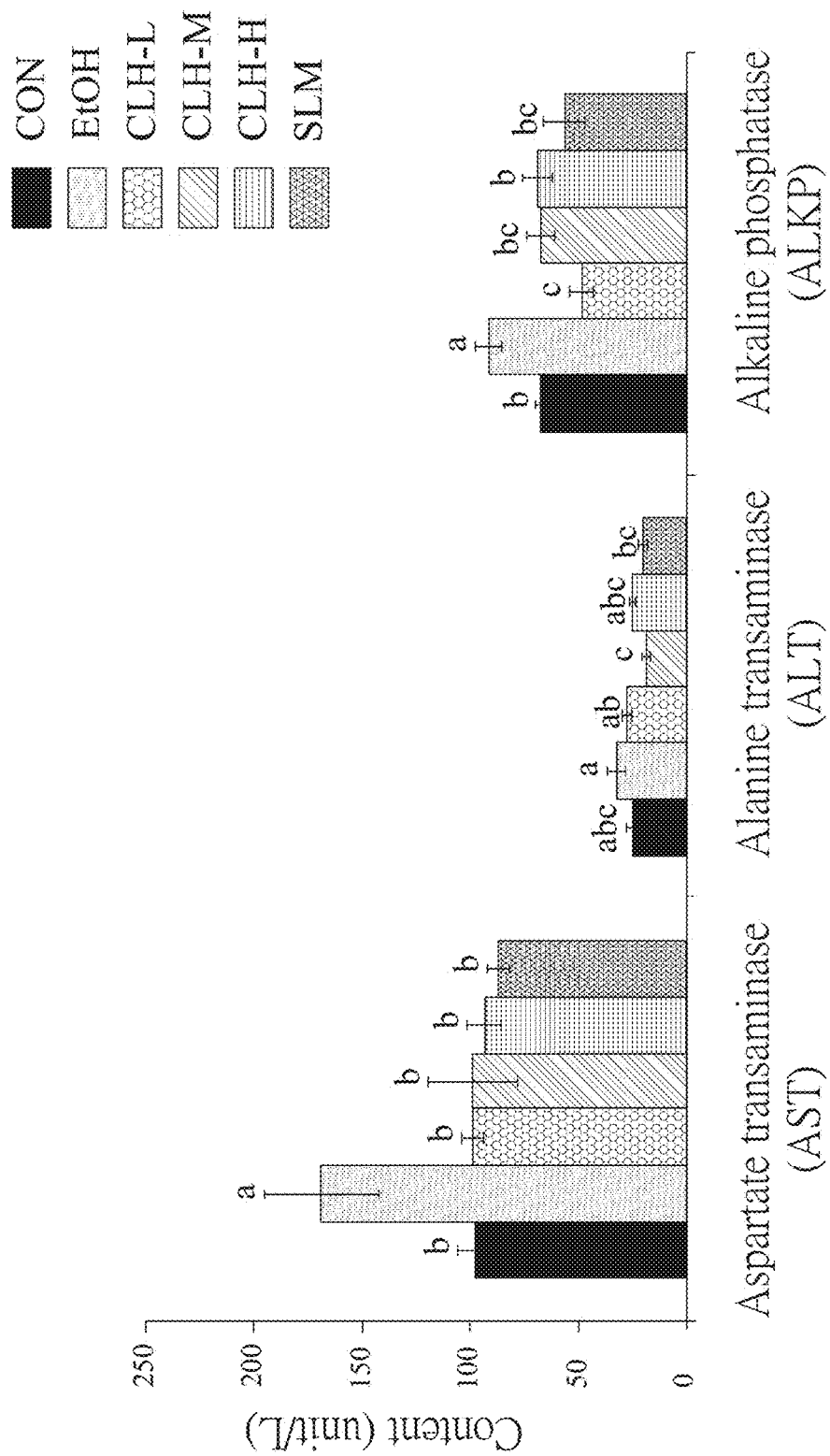
FIG. 1 shows a biochemical index diagram of serum aspartate transaminase (AST), serum alanine transaminase (ALT) and serum alkaline phosphatase (ALKP) levels of mice fed with alcohol liquid diets.

These features and advantages of the present invention will be fully understood and appreciated from the following detailed description of the accompanying drawings.

The present invention provides a composition of chicken liver hydrolysates for improving alcohol metabolism, preventing and treating liver fibrosis. By applying an effective amount to an individual in need, the composition of the chicken liver hydrolysates increases gene expressions and enzyme activities of alcohol metabolism-related enzymes, and decreases collagen deposition, expression of collagen type 1α (Col1a) and α-smooth muscle actin (α-SMA) in liver; in addition, the composition of the chicken liver hydrolysates also decreases expressions of inflammatory factors such as tumor necrosis factor-α (TNF-α), interleukin-6 (IL-6), and transforming growth factor-β (TGF-β). Thus, the composition of the chicken liver hydrolysates of the present invention has the efficacy of liver protection. The chicken liver hydrolysates of the invention comprise from 100 to 200 mg/g of free amino acids. Preferably, the free amino acids comprise from 10 to 20 mg/g of leucine, from 10 to 20 mg/g of lysine, from 10 to 20 mg/g of alanine, and from 15 to 25 mg/g of glutamic acid. In addition, the chicken liver hydrolysates further comprise at least one of taurine, carnosine, and anserine. Preferably, taurine is from 20 to 60 mg/100 g, carcosine is from 10 to 20 mg/100 g, and anserine is from 150 to 250 mg/100 g.

Preferably, the composition of the chicken liver hydrolysates is made as pills, capsules, tablets, powders, oral solution or suspension, and is orally administered to a subject in need.

The present invention will now be described more specifically with reference to the following embodiments, which are provided for the purpose of demonstration rather than limitation.

1. Preparation and Analysis of the Composition of the Chicken Liver Hydrolysates (CLHs)

(1) Preparation of the Composition of the Chicken Liver Hydrolysates

Chicken livers were stored at −20° C. immediately after a collection. Before conducting hydrolyzation, the chicken livers were thawed overnight at 4° C. The fat and the connective tissues of the chicken livers were all removed before hydrolyzation, and the chicken livers were further trimmed into small pieces and weighted. The small pieces of the chicken livers were mixed with double weight of distilled deionized water (ddH$_2$O), and the mixture was homogenized to obtain chicken liver homogenates. The chicken liver homogenates were heated at 95° C. for 15 minutes to inactivate endogenous enzymes, and the chicken liver homogenates were cooled to the room temperature on ice. The chicken liver homogenates were hydrolyzed at 1:400 (w:w) ratio of pepsin (3000 U/mg) to the chicken livers at 37° C., pH2.0 for 2 hours. The reaction was terminated by incubating at 95° C. to inactivate pepsin and cooled to acquire a hydrolysate solution. The hydrolysate solution was centrifuged at 2000 g, 4° C. for 15 minutes, and the supernatant was collected and filtrated by 55 mm filter paper to get a filtrates. The pH value of the filtrates was adjusted to pH7.0, and then lyophilized to obtain the chicken liver hydrolysates (CLHs) of the present invention. The CLHs was store at −20° C.

(2) Analysis of the Composition of the Chicken Liver Hydrolysates

The analysis was entrusted to Food Industry Research and Development Institute (HsinChu, Taiwan). The analytic method is shortly described below: Five grams of a sample was homogenized in 20 mL of 7% (v/v) trichloroacetic acid (TCA) solution for 2 minutes, the mixture was filtered by a 55 mm filter paper to obtain a filtrates and the volume of the filtrates were adjusted to 100 mL by 7% (v/v) TCA solution. Forty microliters of the adjusted filtrates were mixed with equal volume of ethanol to remove TCA and the filtrates-ethanol mixture was concentrated under reduced pressure to remove water, and then the volume was adjusted to 25 mL by ddH$_2$O to obtain a TCA-soluble extract. One milliliter of the TCA-soluble extract was diluted by 0.02N hydroxyl chloride (HCL), filtered by a 0.2 μm filter membrane and analyzed by Hitachi L8800 amino acid analyzer.

The analysis result in Table 1 shows that the concentration of L-leucine, L-lysine, L-alanine, and L-glutamic acid are all higher than 10 mg/g and the concentrations of them are the top four among the free amino acids in the composition of the chicken liver hydrolysates. Furthermore, the composition of the chicken liver hydrolysates also comprise taurine and functional dipeptides such as anserine and carnosine.

TABLE 1

| Free amino acids | Chicken Liver Hydrolysates (mg/100 g powder) |
|---|---|
| L-Leucine | 1128.40 |
| L-Arginine | 717.90 |
| L-Phenylalanine | 579.15 |
| L-Valine | 707.98 |
| L-Lysine | 1068.56 |
| L-Isoleucine | 474.89 |
| L-Methionine | 344.89 |
| L-Theronine | 571.52 |
| Tryptophan | 120.19 |
| L-Histidine | 268.89 |
| Total essential amino acids | 5982.37 |
| L-Alanine | 1001.14 |
| L-Tyrosine | 436.85 |
| L-Serine | 692.34 |
| o-Phosphoserine | 54.77 |
| L-Glutamic acid | 1838.41 |
| L-Aspartic acid | 922.94 |
| Glycine | 597.63 |
| L-Proline | 608.06 |
| L-Ornithine | 134.53 |
| β-Alanine | 39.62 |
| Taurine | 440.07 |
| Total non-essential amino acids | 6766.36 |
| L-Carnosine | 16.94 |
| L-Anserine | 207.16 |

2. Effects of the Composition of the Chicken Liver Hydrolysates on Alcoholic Liver Damage (1) Experimental Animals Forty eight male C57/BL/6J (B6) mice of 8-week old were purchased from the Laboratory Animal Center of National Taiwan University. The body weight of these B6 mice were approximately 19 g to 21 g. Two mice were housed in one cage in an animal room at 22±2° C. with a 12/12 hr light-dark cycle. After one week of acclimation, the mice were randomly divided into 6 groups:

(a) The control group (the CON group): administered with the control liquid diet and 0.2 mL ddH$_2$O by oral gavage.

(b) The ethanol group (the EtOH group): administered with the Lieber-DeCarli regular ethanol diet and 0.2 mL ddH$_2$O by oral gavage.

(c) The composition of the chicken liver hydrolysates with low dosage (The CLH-L group): administered with the Lieber-DeCarli regular ethanol diet and 80 mg/kg-body weight (bw) of the composition of the chicken liver hydrolysates in 0.2 mL ddH$_2$O by oral gavage.

(d) The composition of the chicken liver hydrolysates with medium dossage (The CLH-M group): administered with the Lieber-DeCarli regular ethanol diet and 320 mg/kg-bw of the composition of the chicken liver hydrolysates CLH in 0.2 mL ddH$_2$O by oral gavage.

(e) The composition of the chicken liver hydrolysates with high dosage (The CLH-H group): administered with the Lieber-DeCarli regular ethanol diet and 1280 mg/kg-bw of the composition of the chicken liver hydrolysates in 0.2 mL ddH$_2$O by oral gavage.

(f) The silymarin group (The SLM group): administered with the Lieber-DeCarli regular ethanol diet and 150 mg/kg-bw of silymarin in 0.2 mL ddH$_2$O by oral gavage.

The formulas of the control liquid diet and the Lieber-DeCarli regular ethanol diet are shown in Table 2.

TABLE 2

| Diet | The control liquid diet (g/L) | The Lieber-DeCarli regular ethanol diet (g/L) |
|---|---|---|
| Casein (80 Mesh) | 41.40 | 41.40 |
| DL-Methionine | 0.30 | 0.30 |
| L-Cystine | 0.50 | 0.50 |
| Cellulose | 10.00 | 10.00 |
| Maltose dextrin | 115.20 | 25.60 |
| Corn oil | 8.50 | 8.50 |
| Olive oil | 28.40 | 28.40 |
| Safflower oil | 2.70 | 2.70 |
| Mineral Mix #210011 | 8.75 | 8.75 |
| Vitamin Mix #310011 | 2.50 | 2.50 |
| Choline bitartrate | 0.53 | 0.53 |
| Xanthan gum | 3.00 | 3.00 |
| Ethanol | 0 | 67.00 |
| Note | This diet contains 1.0 Kcal/mL, of which 35% are fat derived, 47% are derived from carbohydrate, and 18% are derived from protein. | This diet contains 1.0 Kcal/mL, of which 35% are fat derived, 11% derived from carbohydrate, 18% derived from protein and 36% are derived from ethanol. |

The animal experiment lasted for 8 weeks; the body weight of each mouse was recorded at the beginning and the end of the experiment. The daily liquid feed (mL) intakes as a food intake of each mouse was calculated. Mice were sacrificed after 8 weeks and the blood, heart, kidney, epididymal fat tissue, and perirenal fat tissue were all collected, weighted and then stored at −80° C. for further analysis.

The experiment was conducted by a complete randomized design. The raw data was presented as "mean±standard error of the mean (SEM)". The data was analyzed by one way-analysis of variance (ANOVA) and Fisher's Least Significant Different test to distinguish significant differences among groups. All statistical analysis of data was performed by SAS9.2 software (SAS Institute Inc, Cary, N.C., USA). If there is no significant difference between two groups, these groups were labeled with one identical letter. If an experimental group was labeled with two letters, for example, labeled with "ab", which means this group does not differ from a group labeled with "a", and also does not differ from another groups labeled with "b".

(2) Effect of the Composition of the Chicken Liver Hydrolysates on Experimental Animals (i) Relative Sizes of Organs and Tissues No significant differences (p>0.05) of the daily food intake and the body weight are observed among all groups during the 8-week experimental period (data not shown). The relative sizes of the organs and adipose tissue is presented in Table 3. In all groups, there are no differences in the relative sizes of heart and kidney, but the relative sizes of liver and spleen are increased in the EtOH group compared to those of the CON group (p<0.05). The relative sizes of spleen, perirenal fat tissue and epididymal fat tissue are apparently decreased in mice supplement with the chicken liver hydrolysates and silymarin (the CLH-L group, the CLH-M group, the CLH-H group and the SLM group) compared to mice of the EtOH group (p<0.05).

TABLE 3

| | Relative size (g/100 g-bw) | | | | | |
|---|---|---|---|---|---|---|
| | CON | EtOH | CLH-L | CLH-M | CLH-H | SLM |
| Heart | 0.45 ± 0.01$^{ab}$ | 0.45 ± 0.01$^{ab}$ | 0.45 ± 0.01$^{ab}$ | 0.48 ± 0.02$^{a}$ | 0.44 ± 0.01$^{b}$ | 0.45 ± 0.01$^{ab}$ |
| Liver | 4.09 ± 0.06$^{b}$ | 4.46 ± 0.06$^{a}$ | 4.30 ± 0.14$^{ab}$ | 4.40 ± 0.10$^{a}$ | 4.19 ± 0.08$^{ab}$ | 4.45 ± 0.06$^{a}$ |
| Kidney | 1.18 ± 0.01$^{b}$ | 1.22 ± 0.02$^{ab}$ | 1.18 ± 0.01$^{b}$ | 1.25 ± 0.02$^{a}$ | 1.18 ± 0.03$^{b}$ | 1.19 ± 0.04$^{ab}$ |
| Spleen | 0.18 ± 0.00$^{b}$ | 0.21 ± 0.01$^{a}$ | 0.18 ± 0.01$^{b}$ | 0.18 ± 0.00$^{b}$ | 0.18 ± 0.00$^{b}$ | 0.18 ± 0.01$^{b}$ |
| Perirenal fat tissue | 0.30 ± 0.05$^{b}$ | 0.52 ± 0.04$^{a}$ | 0.32 ± 0.03$^{b}$ | 0.34 ± 0.04$^{b}$ | 0.31 ± 0.04$^{b}$ | 0.37 ± 0.04$^{b}$ |

TABLE 3-continued

| | Relative size (g/100 g-bw) | | | | | |
|---|---|---|---|---|---|---|
| | CON | EtOH | CLH-L | CLH-M | CLH-H | SLM |
| Epididymal fat tissue | $1.40 \pm 0.10^c$ | $2.29 \pm 0.10^a$ | $1.87 \pm 0.21^b$ | $1.79 \pm 0.13^{bc}$ | $1.73 \pm 0.16^{bc}$ | $1.68 \pm 0.15^{bc}$ |

(ii) Biochemical Indexes of Livers

Aspartate transaminase (AST) and alanine transaminase (ALT) are rich in liver and may be released into blood when the liver is damaged. Alkaline phosphatase (ALKP) is produced by liver, bone and placenta, and is secreted into bile through liver. Accordingly, the levels of AST, ALT and ALKP in sera can be used to estimate the function of liver and gallbladder.

As shown in FIG. 1, there were no differences between serum ALT in the CON group and the EtOH group ($p>0.05$), but the concentration of AST and ALKP are significantly higher in the EtOH group compared to the CON group ($p<0.05$). The supplementation of the chicken liver hydrolysates (the CLH-L group, the CLH-M group and the CLH-H group) decreases the serum AST and serum ALKP significantly ($p<0.05$).

Figure 2:
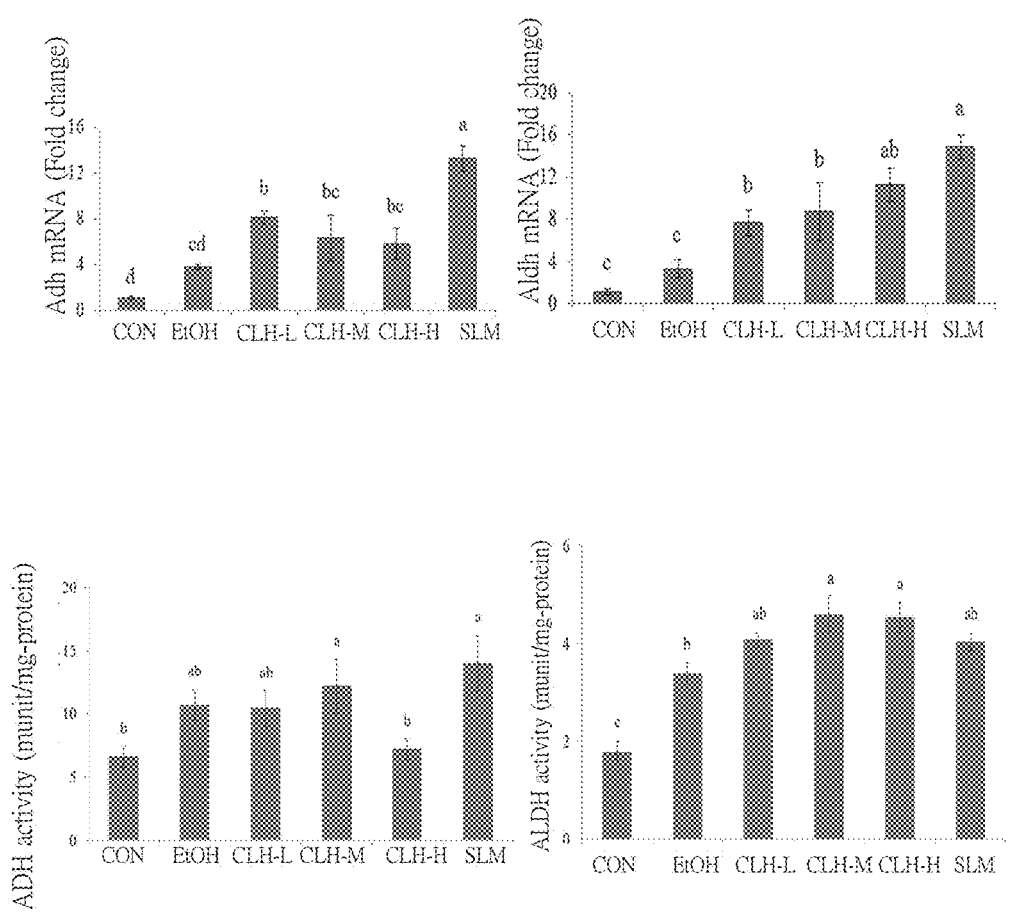
FIG. 2 shows diagrams of expressions and activities of alcohol dehydrogenase and aldehyde dehydrogenase in livers of mice fed with alcohol liquid diets.

(iii) Effect of the Composition of the Chicken Liver Hydrolysates on Ethanol Metabolism The gene expressions of alcohol dehydrogenase (Adh) and aldehyde dehydrogenase (Aldh) are detected to evaluate the effect of the composition of the chicken liver hydrolysates on ethanol metabolism. As shown in FIG. 2, the expressions of Adh and Aldh are slightly increased in the EtOH group compared to the CON group, and the expressions of Adh and Aldh are significantly upregulated in the CLH supplemented groups (the CLH-L group, the CLH-M group, and the CLH-H group) compared to the CON group and the EtOH group ($p<0.05$). In addition, the enzymatic activities of alcohol dehydrogenase and aldehyde dehydrogenase are significantly increased in the EtOH group compared to the CON group, and the activity of aldehyde dehydrogenase is significantly increased in the CLH-M group and the CLH-L group compared to the EtOH group ($p<0.05$).

(iv) Histopathological Examination

Figure 3A:
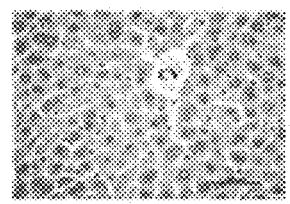
FIG. 3(A) shows microscopic photographs of liver sections stained with haematoxylin and eosin in mice fed with alcohol liquid diets.
Figure 3A:
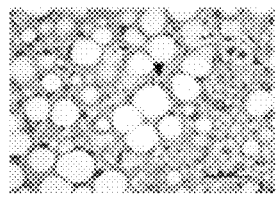
Figure 3A:
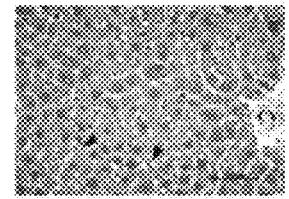
Figure 3A:
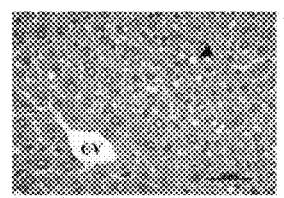
Figure 3A:
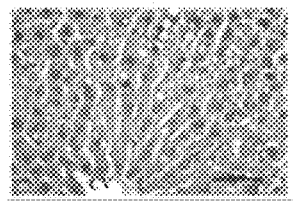
Figure 3A:
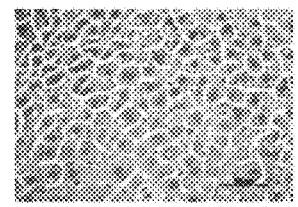

The biopsies of mouse liver were sliced and stained by hematoxylin and eosin, and the histology of livers are examined. As shown in FIG. 3(A), the appearances of hepatocytes are polygonal as ordinary hepatocytes and arranged around the central vein (CV) in the CON group. In the EtOH group, a lot of lipid drops are observed which represent a typical characteristic of macrovesicular fatty livers. However, in the CLH groups (the CLH-L group, the CLH-M group and the CLH-H group) and the SLM group, the appearances of hepatocytes are quite similar to the CON group. Furthermore, the hepatic steatosis is evaluated in a double blind assay according to the steatosis score. The scoring criteria are shown in table 4 which is categorized into 4 groups according to the proportion of hepatocytes involved in steatosis.

TABLE 4

| Proportion of hepatocytes involved in steatosis | Steatosis score |
|---|---|
| <5% hepatocytes involved | 0 |
| 5~33% hepatocytes involved | 1 |
| 33~66% hepatocytes involved | 2 |
| >66% hepatocytes involved | 3 |

Figure 3B:
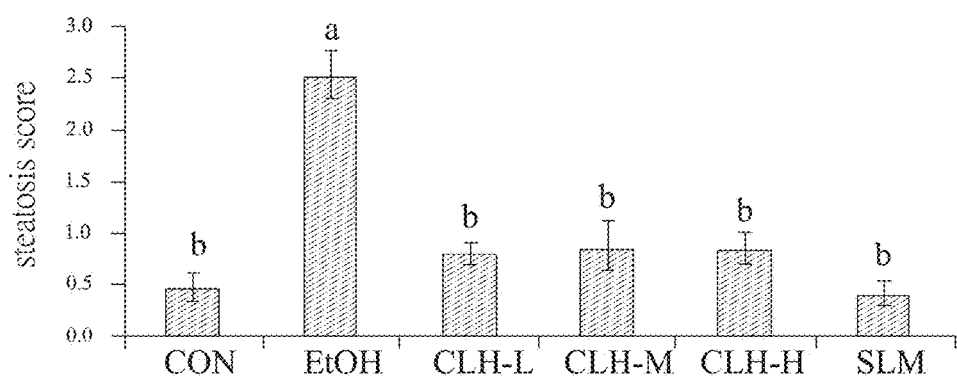
FIG. 3(B) shows a diagram of liver steatosis score in mice fed with alcohol liquid diets.

In FIG. 3(B), the steatosis score is significantly higher in the EtOH group than in the CON group ($p<0.05$). However, in the CLH groups, the steatosis scores are significantly lower than in the EtOH group ($p<0.05$), and are even not differenet from that in the CON group ($p>0.05$).

(v) Lipid Content in Sera and Livers

Figure 4:
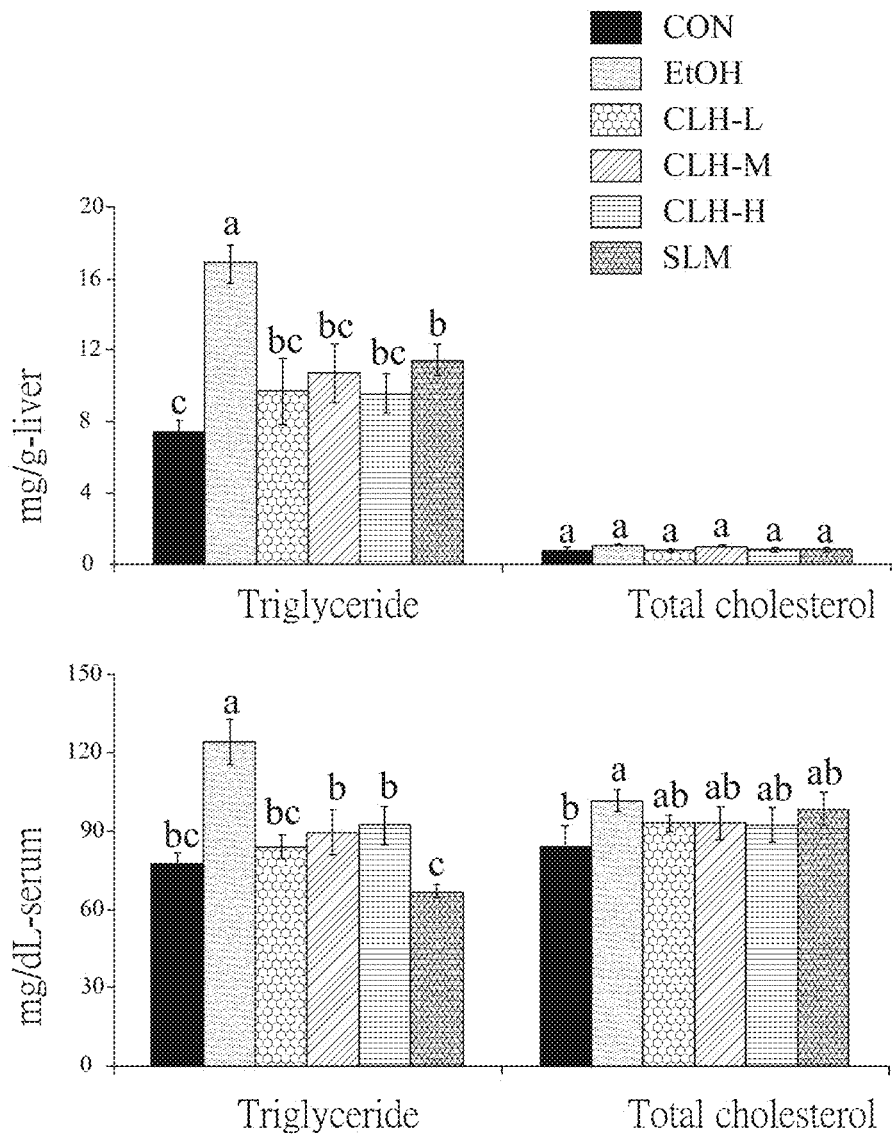
FIG. 4 shows diagrams of contents of liver triglyceride and total cholesterol, as well as serum triglyceride and total cholesterol in mice fed with alcohol liquid diets.

The lipid contents in sera and livers were further examined. As shown in FIG. 4, the triglyceride (TG) contents in sera and livers aresignificantly higher in the EtOH group than those in the CON group ($p<0.05$), but the TG contents are significantly lower in the CLH supplemented groups (the CLH-L, the CLH-M group, and the CLH-H group) ($p<0.05$). Moreover, the total cholesterol contents in sera are increased in the EtOH group, but supplementation with the composition of the chicken liver hydrolysates has no effect on total cholesterol contents in sera ($p>0.05$). The total cholesterol contents in livers have no significant differences among all groups ($p>0.05$).

(vi) Antioxidative Ability of Sera and Livers

To evaluate the antioxidative ability of the composition of the chicken liver hydrolysates, the $ABTS^+$ free radical clearing ability is tested and represented as trolox equivalent antioxidant capacity (TEAC). The lipid peroxidation is also determined by thiobarbituric acid reactive substance (TBARS) value.

According to Table 5, the TEAC values in sera and livers of the EtOH group are significantly lower ($p<0.05$) than in the CON group, but the TEAC values of the CLH groups (the CLH-L group, the CLH-M group, and the CLH-H group) are elevated significantly ($p<0.05$). The TBARS values in sera and livers are significantly increased in the EtOH group compared to those in the CON group ($p<0.05$), and those TBARS values of the CLH-M group and the CLH-H group are significant lower than those in the EtOH group.

TABLE 5

| | TEAC | | TBARS | |
|---|---|---|---|---|
| | Serum (nmole/mL) | Liver (nmole/mg-protein) | Serum (nmole MDA eq./mL) | Liver (nmole MDA eq./mg-protein) |
| CON | $4.12 \pm 0.02^c$ | $145.07 \pm 2.85^b$ | $19.44 \pm 1.79^d$ | $0.49 \pm 0.03^b$ |
| EtOH | $2.84 \pm 0.14^d$ | $118.34 \pm 2.74^c$ | $68.93 \pm 1.87^a$ | $0.79 \pm 0.10^a$ |
| CLH-L | $4.28 \pm 0.11^b$ | $152.01 \pm 6.48^b$ | $61.21 \pm 2.11^{ab}$ | $0.59 \pm 0.06^{ab}$ |
| CLH-M | $4.62 \pm 0.07^a$ | $145.01 \pm 6.54^b$ | $54.01 \pm 5.43^{bc}$ | $0.45 \pm 0.02^b$ |
| CLH-H | $4.51 \pm 0.04^b$ | $158.25 \pm 3.88^b$ | $48.30 \pm 6.34^c$ | $0.45 \pm 0.05^b$ |
| SLM | $4.48 \pm 0.18^b$ | $294.16 \pm 14.82^a$ | $52.62 \pm 2.26^{bc}$ | $0.64 \pm 0.12^{ab}$ |

Figure 5:
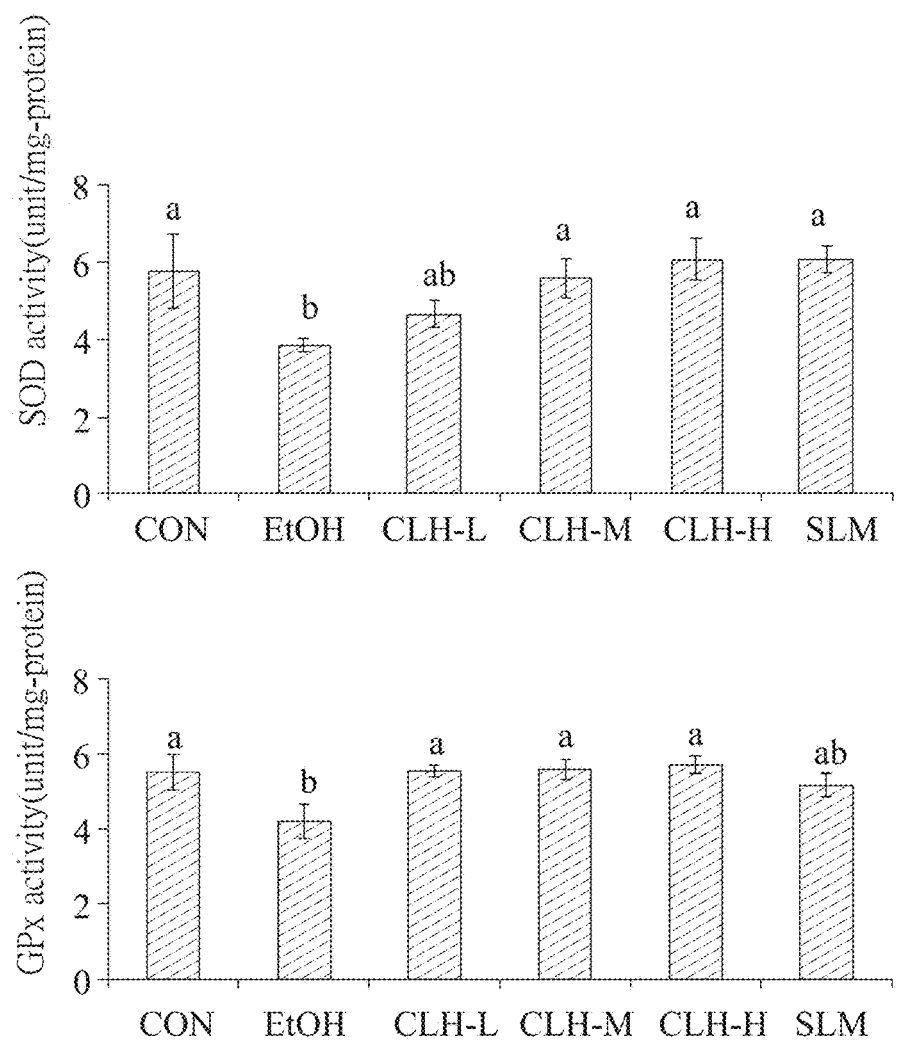
FIG. 5 shows diagrams of activities of superoxide dismutase (SOD) and glutathione peroxide (GPx) in livers of mice fed with alcohol liquid diets.

The enzymatic activities of superoxide dismutase (SOD) and glutathione peroxide (GPx) are also examined to assess the anti-oxidation system of livers. In FIG. 5, the enzymatic activities of SOD and GPx in the EtOH group are decreased significantly compared to the CON group (p<0.05). However, the SOD activity is significantly up-regulated in the CLH-M group and the CLH-H group compared to that of the EtOH group (p<0.05), but CLH supplementation increases the GPx activity in ethanol liquid diet fed mice. The results indicated that the composition of the chicken liver hydrolysates of the present invention improves the anti-oxidative ability of livers.

2. Effect of the Composition of the Chicken Liver Hydrolysates on Liver Ribrosis (1) Experimental Animals Forty male Wistar rats of 5-week old were purchased from BioLASCO Taiwan Co., Ltd. (Taipei, Taiwan). Two rats were housed in one cage in an animal room at 22±2° C. with a 12/12 h light-dark cycle. After one week of acclimation, the mice were randomly divided into 5 groups:

(a) The control group (The CON group): intraperitoneal injection of 0.3 mL normal saline, and administration of 0.5 mL $ddH_2O$ by oral gavage;

(b) The thioacetamide group (The TAA group): intraperitoneal injection of 100 mg TAA/kg-body weight (bw) in 0.3 mL $ddH_2O$ and administration of 0.5 mL $ddH_2O$ by oral gavage;

(c) The composition of the chicken liver hydrolysates with low dosage (The CLH-L group): intraperitoneal injection of 100 mg TAA/kg-bw in 0.3 mL $ddH_2O$ and administration of 200 mg/kg-bw CLH in 0.5 mL $ddH_2O$ by oral gavage;

(d) The composition of the chicken liver hydrolysates with high dosage (The CLH-H group): intraperitoneal injection of 100 mg TAA/kg-bw in 0.3 mL $ddH_2O$ and administration of 600 mg/kg-bw CLH in 0.5 mL $ddH_2O$ by oral gavage; and (e) The carnosine group (The CNS group): intraperitoneal injection of 100 mg TAA/kg-bw in 0.3 mL $ddH_2O$ and administration of 200 mg/kg-bw carnosine in 0.5 mL $ddH_2O$ by oral gavage;

The experiment lasted for 10 weeks. The rats were injected with $ddH_2O$ or TAA intraperitoneally once a week and administered of $ddH_2O$, the composition of the chicken liver hydrolysates or carnosine every day. One kilogram of the chow diet comprises 487 g carbohydrate, 239 g protein, 50 g fat, 51 g fibre and 70 g ash (Laboratory Rodent Diet 5001, PMI Nutrition International/Purina Mills LLC, Richmond, Ind., USA). All rats were fasted overnight before euthanized at the last day of experiment, the organs and the tissues were collected and weighted, and stored at −80° C. for further analysis.

The experiment was conducted by a complete randomized design. The raw data was expressed as "mean±SEM". The data was analyzed by analysis of variance (ANOVA) and Fisher's Least Significant Different (LSD) test was used to distinguish significant differences among groups. All statistical analysis of the data was performed by SAS9.2 software (SAS Institute Inc, Cary, N.C., USA). If there is no significant difference between two groups, these groups werelabeled with one identical letter. If an experimental group was labeled with two letters, for example, labeled with "ab", which means this group does not differ from a group labeled with "a", and does not differ from another groups labeled with "b".

(2) Effects of the Composition of the Chicken Liver Hydrolysates (CLH) on Experimental Animals (i) Body Weight and Feed Efficiency Table 6 shows body weight and feed efficiency of all groups. The "weight increase" of the TAA group is significantly lower than in the CON group (p<0.05) and supplementation of the composition of the chicken liver hydrolysates does not restore the "weight increase" (p>0.05). The food intake of the CLH groups decreased significantly compared to the CON group or the TAA group (p<0.05). Cotreatment of CLHs tended to improve feed efficiency compared to TAA group. There were no significant differences on water intakes among groups (p>0.05).

TABLE 6

| | CON | TAA | CLH-L | CLH-H | CNS |
|---|---|---|---|---|---|
| Initial body weight (g) | 212.07 ± 2.64$^a$ | 215.08 ± 3.34$^a$ | 213.95 ± 2.14$^a$ | 216.76 ± 3.57$^a$ | 216.62 ± 4.63$^a$ |
| Final body weight (g) | 451.30 ± 5.70$^a$ | 362.90 ± 9.37$^b$ | 366.51 ± 6.83$^b$ | 362.11 ± 6.42$^b$ | 380.61 ± 10.47$^b$ |
| Weight increase (g) | 239.22 ± 4.02$^a$ | 147.82 ± 10.41$^b$ | 152.56 ± 5.64$^b$ | 145.36 ± 5.72$^b$ | 163.99 ± 7.63$^a$ |
| Food intake (g/rat/day) | 29.12 ± 0.29$^a$ | 29.54 ± 0.92$^a$ | 26.81 ± 0.36$^b$ | 24.49 ± 0.44$^c$ | 28.43 ± 0.50$^{ab}$ |
| Feed efficiency (%) | 11.78 ± 0.22$^a$ | 7.58 ± 0.60$^c$ | 8.38 ± 0.31$^{bc}$ | 8.59 ± 0.47$^{bc}$ | 8.89 ± 0.33$^b$ |
| Water intake (mL/rat/day) | 46.55 ± 1.76$^a$ | 44.75 ± 1.63$^a$ | 41.48 ± 3.21$^a$ | 40.39 ± 2.15$^a$ | 44.70 ± 4.68$^a$ |

(ii) Relative Sizes of Organs and Tissues

Table 7 shows the relative sizes of organs or perirenal fat tissue of all groups. The relative sizes of liver, kidney and spleen of the TAA group are increased significantly compared to those of the CON group (p<0.05) and supplementation of the composition of the chicken liver hydrolysates or carnosine does not decrease the relative sizes of liver, kidney and spleen (p>0.05). The relative sizes of heart and perirenal fat tissue have no significant differences among all groups (p>0.05).

TABLE 7

| | Relative size (g/100 g-bw) | | | | |
|---|---|---|---|---|---|
| | CON | TAA | CLH-L | CLH-H | CNS |
| Liver | 2.94 ± 0.08[b] | 4.31 ± 0.13[a] | 4.09 ± 0.09[a] | 4.15 ± 0.16[a] | 4.14 ± 0.09[a] |
| Heart | 0.30 ± 0.00[a] | 0.29 ± 0.00[a] | 0.30 ± 0.01[a] | 0.30 ± 0.01[a] | 0.31 ± 0.01[a] |
| Kidney | 0.63 ± 0.01[b] | 0.80 ± 0.02[a] | 0.74 ± 0.04[a] | 0.76 ± 0.01[a] | 0.74 ± 0.01[a] |
| Spleen | 0.19 ± 0.01[b] | 0.33 ± 0.02[a] | 0.29 ± 0.01[a] | 0.32 ± 0.01[a] | 0.31 ± 0.02[a] |
| Perirenal fat | 1.42 ± 0.12[a] | 1.18 ± 0.08[a] | 1.02 ± 0.15[a] | 1.09 ± 0.17[a] | 1.47 ± 0.11[a] |

(iii) Biochemical Indexes of Livers

Table 8 shows the biochemical indexes of liver in sera of each group. The contents of AST and ALT increase significantly in the TAA group (p<0.05), but decrease in the CLH-H group compared to those in the TAA group. The significant decreased levels of total protein and triglyceride in the TAA group (p<0.05) might be caused by liver damage since liver is the major source of serum proteins and endogenous triglyceride. The contents of total cholesterol and blood urea nitrogen have no differences among all groups (p>0.05).

TABLE 8

| | CON | TAA | CLH-L | CLH-H | CNS |
|---|---|---|---|---|---|
| AST (U/L) | 250.00 ± 19.56[b] | 325.00 ± 24.50[a] | 335.00 ± 13.54[a] | 234.63 ± 16.08[b] | 211.00 ± 24.57[b] |
| ALT (U/L) | 63.88 ± 11.16[b] | 93.25 ± 5.28[a] | 83.75 ± 3.00[ab] | 66.38 ± 6.95[b] | 63.88 ± 5.86[b] |
| Total protein (g/dL) | 5.48 ± 0.26[a] | 4.15 ± 0.20[b] | 4.69 ± 0.14[b] | 4.66 ± 0.19[b] | 4.26 ± 0.24[b] |
| Triglyceride (mg/dL) | 51.50 ± 4.64[a] | 28.75 ± 1.97[b] | 33.88 ± 2.46[b] | 29.88 ± 1.84[b] | 33.25 ± 3.19[b] |
| Total cholesterol (mg/dL) | 57.63 ± 3.31[a] | 47.50 ± 3.73[a] | 57.13 ± 2.43[a] | 53.88 ± 2.06[a] | 52.38 ± 3.53[a] |
| Blood urea nitrogen (g/dL) | 15.38 ± 0.50[a] | 16.88 ± 1.30[a] | 16.88 ± 0.93[a] | 15.88 ± 0.79[a] | 15.38 ± 0.89[a] |

(iv) Histopathological Examination

Figure 6:
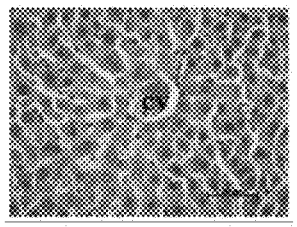
FIG. 6 shows microscopic photographs of liver sections stained with haematoxylin and eosin of thioacetamide (TAA)-treated mice.
Figure 6:
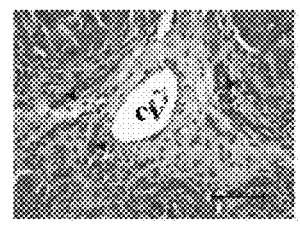
Figure 6:
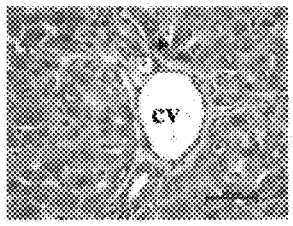
Figure 6:
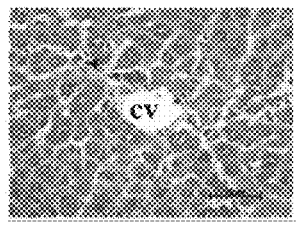
Figure 6:
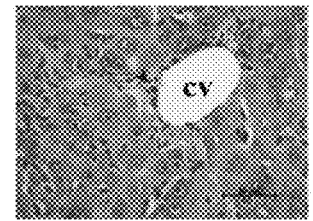

The biopsies of rat livers were sliced and stained by hematoxylin and eosin, and the histology of livers are examined. As shown in FIG. 6, the appearances of hepatocytes are polygonal as ordinary hepatocytes and arranged around the central vein (CV) in the CON group. In the TAA group, a lot of non-hepatic infiltrating cells around the CV are observed, and the arrangement of hepatocytes become disordered. However, in the CLH groups, especially in the CLH-H group, the infiltrating cells are decreased and the appearances of hepatocytes are similar to the CON group.

(v) Collagen Deposition in Livers

Figure 7A:
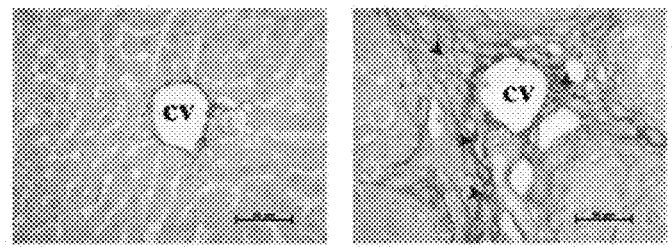
FIG. 7(A) shows microscopic photographs of liver section stained with Sirius red of thioacetamide (TAA)-treated mice.
Figure 7A:
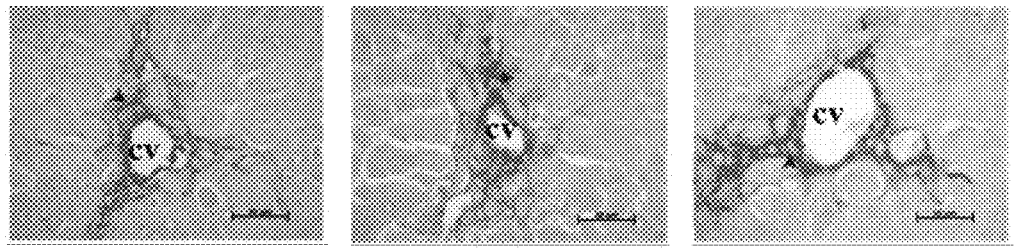
Figure 7B:
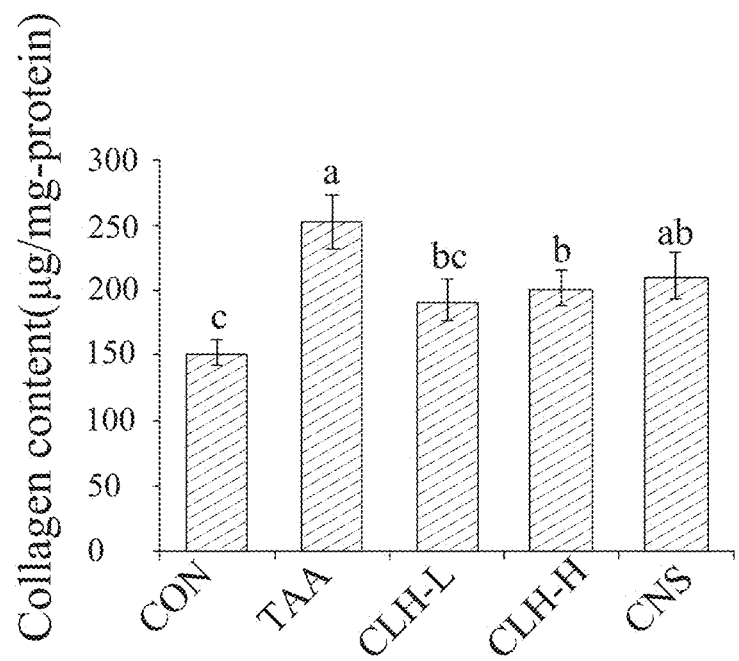
FIG. 7(B) shows diagrams of collagen deposition in livers of thioacetamide (TAA)-treated mice.
Figure 8:
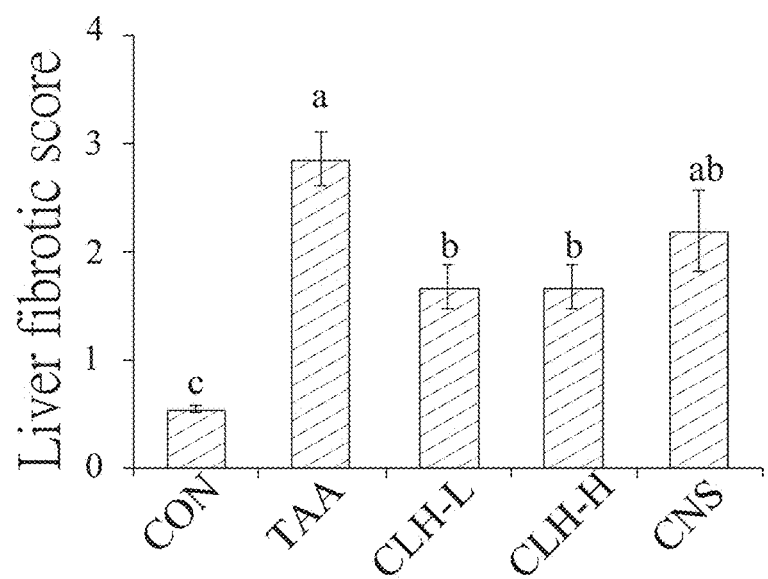
FIG. 8 shows a diagram of the liver fibrotic index of thioacetamide (TAA)-treated mice.

Sirius red dye can bind to the helical structure of the collagen, and thus the Sirius red stain assay can be used to examine the deposition of collagen in livers. Furthermore, liver collagen levels of the mice are also determined by using commercial kits (Chondres Inc., Redmond, Wash., USA). The protocol is briefly describes below: (i) a sample is homogenates with 0.05M acetic acid followed by adding pepsin solution (1 mg/mL in 0.05M acetic acid) to obtain a first mixture; (ii) the first mixture is incubated at 4° C. for 72 hours with gentle mixing, then centrifuged at 2000 g for 3 minutes and stored at −20° C. in tubes pre-treated with horse serum to obtain a second mixture; (iii) the second mixture is diluted and reacted with Sirius dye for 20 minutes, and then centrifuged to separate a red precipitant followed by adding a washing solution and centrifuging; (iv) the red precipitant is dissolved by a extraction buffer, and the absorbance at 530 nm is detect. The collagen content in the sample is calculated by using a standard curve plotted by bovine Type I collagen and expressed as μg/mg-protein. As shown in FIG. 7(A), the collagen is only detected around the CV in the CON group. In the TAA group, large scale of collagen deposition is detected, but the collagen deposition is remarkably decreased in the CLH supplemented groups (the CLH-L and CLH-H group) and carnosine supplemented group (the CNS group). In FIG. 7(B), the liver collagen content is significantly higher in the TAA group than in the CON group, but the liver collagen contents are significantly decreased in the CLH supplemented groups (the CLH-L group and the CLH-H group) and carnosine supplemented group (the CNS group) compared to that in the TAA group. In addition, the fibrotic score is also evaluated by the METAVIR scoring system to represent the severity of liver fibrosis. In FIG. 8, the liver fibrotic score of the TAA group is significantly higher than that in the CON group (p<0.05), and supplementation of the composition of the chicken liver hydrolysates could decrease the fibrotic score.

(vi) Expressions of Inflammation-Related and Fibrosis-Related Genes

Figure 9:
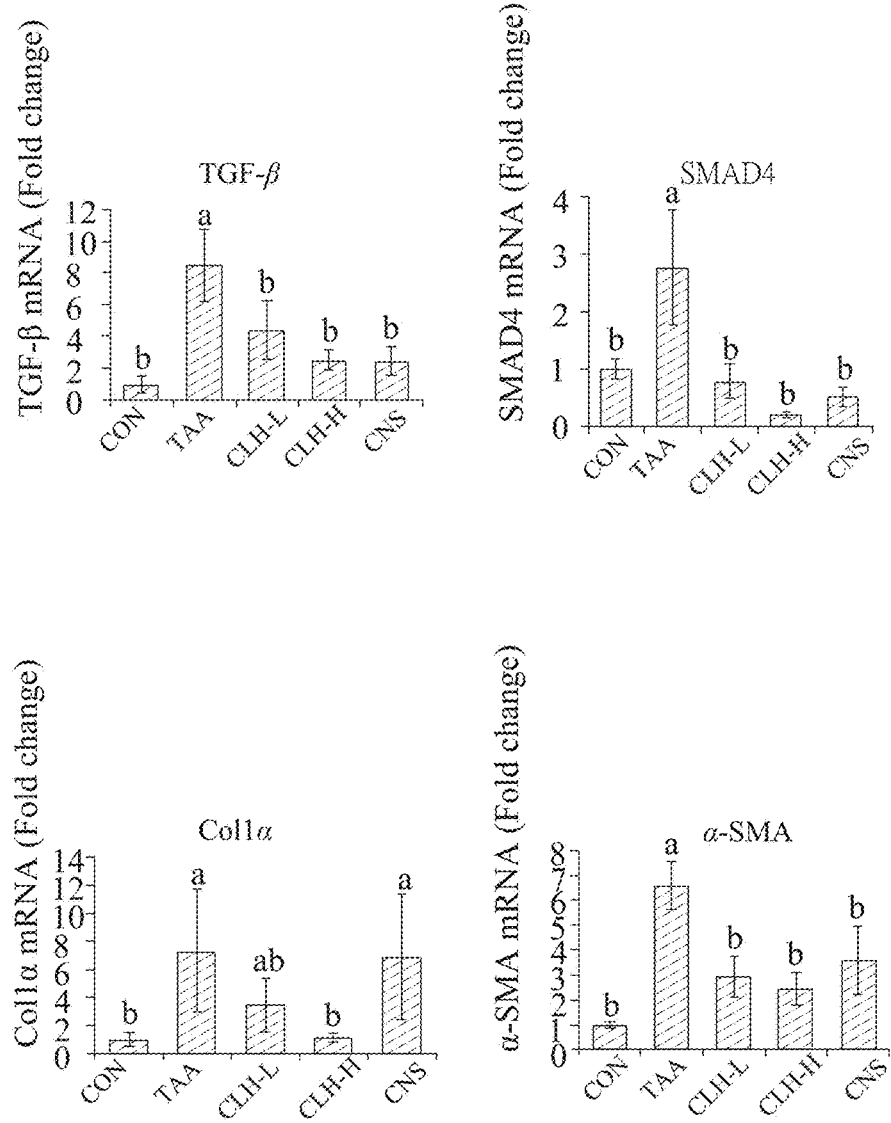
FIG. 9 shows diagrams of gene expressions of TGF-β, SMAD4, Col1a, and α-SMA in livers of thioacetamide (TAA)-treated mice.

A repeated damage and repair of liver tissues leads to an alternation of liver extracellular matrix (ECM) composition, including increasing of collagen deposition and twined collagen-constituted scar tissues, and at last become cirrhosis. During the process of ECM alternation, inflammation-related cytokines might be involved. For example, TGF-β activates the genes of connective tissue growth factor (CTGF), collagen type I α (Col1α) or α-smooth muscle actin (α-SMA) through SMAD protein. To investigate the effect of the composition of the chicken liver hydrolysates on liver fibrosis, the expressions of TGF-β, SMAD4, Col1α and α-SMA are examined by quantitative reverse transcription-polymerase chain reaction (qRT-PCR). As shown in FIG. 9, the expressions of TGF-β, SMAD4, Col1α and α-SMA are significantly higher in the TAA group than those in the CON group (p<0.05). In the CLH supplemented groups, especially in the CLH-H group, the expressions of TGF-β, SMAD4, Colα and α-SMA are significantly decreased compared to those of TAA group (p<0.05).

(vii) Anti-Oxidative Ability of Livers

Oxidative stress or free radicals also induce liver damage and inflammation, and a prolongation an exposure to the oxidative stress may also lead to liver fibrosis. An anti-oxidative ability of liver is estimated by clearance of ABTS$^+$ free radical and represented as trolox equivalent antioxidant capacity (TEAC). In addition, lipid peroxidation status is also evaluated by thiobarbituric acid reactive substance (TBARS).

Figure 10:
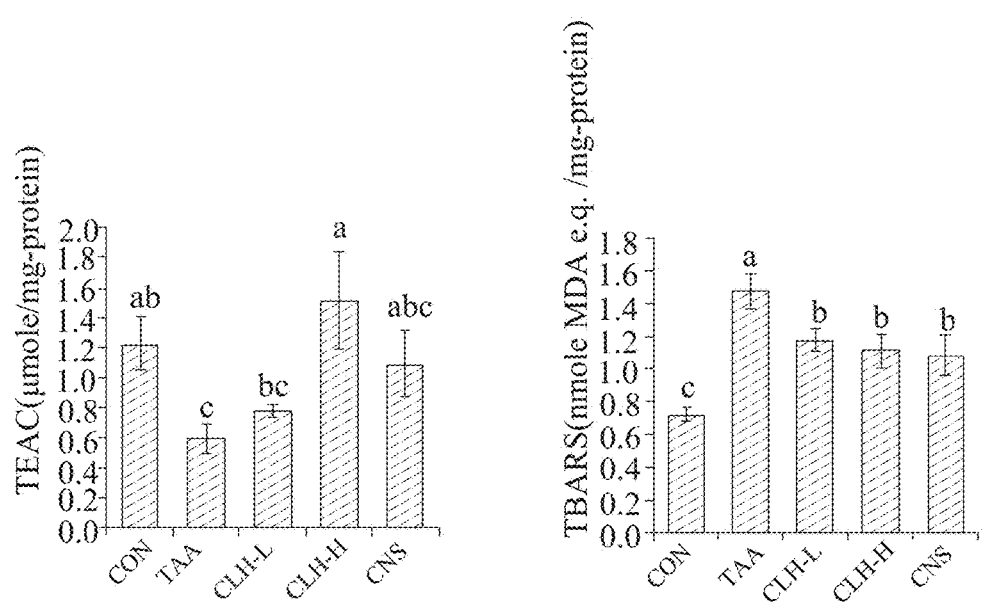
FIG. 10 shows diagrams of anti-oxidative abilities in the livers of thioacetamide (TAA)-treated mice.

As shown in FIG. 10, in TAA group, the anti-oxidative ability of is decreased and the lipid peroxidation is increased significantly (p<0.05) compared to those the CON group, respectively. However, supplemented with the composition of the chicken liver hydrolysates, especially supplemented with high-dosage of the composition of the chicken liver hydrolysates (the CLH-H group), increase anti-oxidative ability of livers and decrease lipid peroxidation in livers significantly compared to the TAA group (p<0.05).

(viii) Expressions of Inflammation-Related Factors

Figure 11:
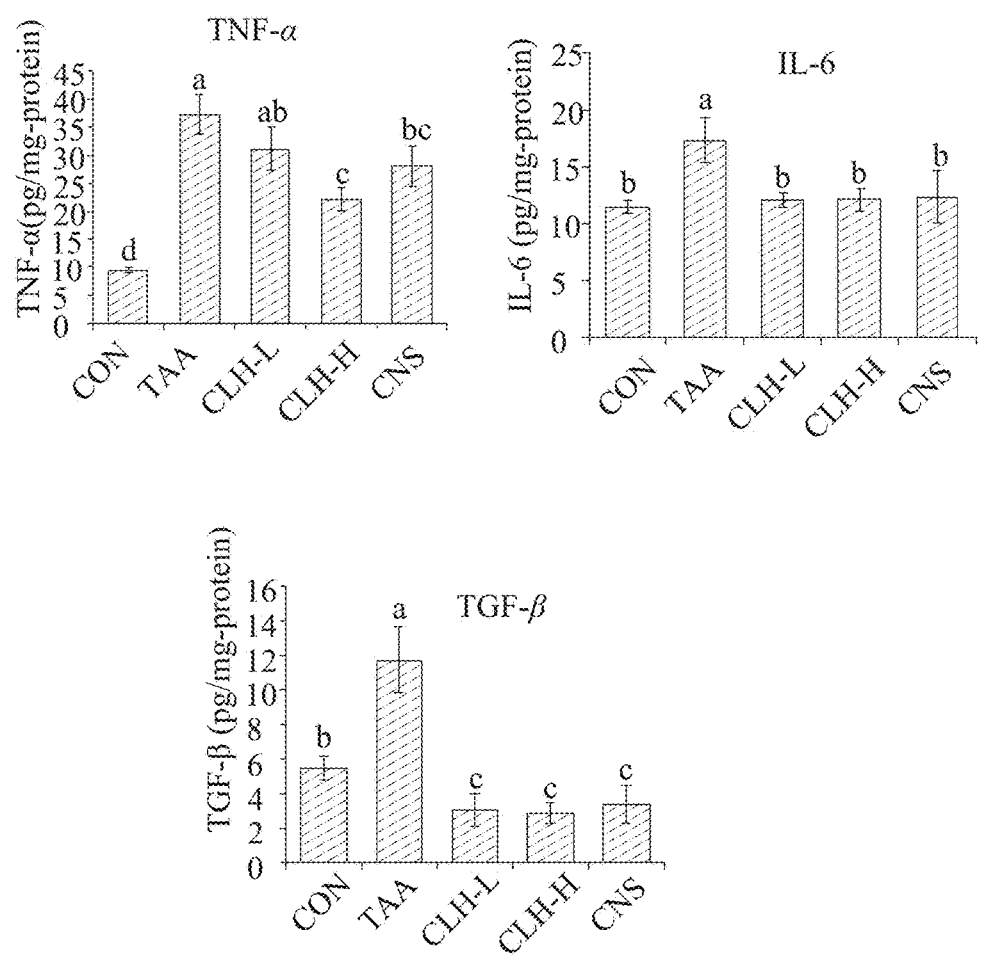
FIG. 11 shows diagrams of protein expressions of TNF-α, IL-6 and TGF-β in livers of thioacetamide (TAA)-treated mice.

Enzyme-linked immunosorbent assay (ELISA) was used to determine the expressions of inflammation-related factors in liver. As shown in FIG. 11, expressions of TNF-α, IL-6, and TGF-β are significantly higher in the TAA group than in the CON group (p<0.05). In the CLH supplemented groups, especially in the CLH-H group, the expressions of TNF-α, IL-6 and TGF-β is significantly lower than those in the TAA group (p<0.05). The results indicated that the composition of the chicken liver hydrolysates of the present invention has the efficacy to down-regulate inflammation.

According to the above description and embodiments, the use of the composition of the chicken liver hydrolysates of the present invention has the advantages as following:

1. The composition of the chicken liver hydrolysates comprises plenty of free amino acids and functional dipeptides (carnosine and anserine).
2. The composition of the chicken liver hydrolysates improves alcohol metabolism by increasing the expression and the activity of alcohol dehydrogenase and aldehyde dehydrogenase.
3. The composition of the chicken liver hydrolysates improves lipid metabolism by decreasing triglyceride in livers and in sera.
4. The composition of the chicken liver hydrolysates decreases the expressions of fibrosis-related genes, e.g. Colα or α-SMA, and decreases collagen deposition in livers to alleviate liver fibrosis.
5. The composition of the chicken liver hydrolysates decreases oxidative stress and lipid peroxidation, and increases the activities of anti-oxidation enzymes, e.g. SOD or GPx.
6. The composition of the chicken liver hydrolysates decreases the expressions of TNF-α, IL-6 and TGF-β thus has the potential to regulate immune response.

What is claimed is:

1. A method of improving alcohol metabolism, preventing or reducing liver fibrosis in an individual in need thereof, comprising administering to the individual in need thereof a composition of chicken liver hydrolysates comprising from 100 to 200 mg/g of free amino acids, wherein the fire amino acids comprise from 10 to 20 mg/g of leucine, from 10 to 20 mg/g of lysine, from 10 to 20 mg/g of alanine, and from 15 to 25 mg/g of glutamic acid.

2. The method as claimed in claim 1, wherein the free amino acids comprise 11.28 mg/g of leucine, 10.68 mg/g of lysine, 10.01 mg/g of alanine, and 18.38 mg/g of glutamic acid.

3. The method as claimed in claim 1, wherein the composition of the chicken liver hydrolysates further comprises at least one of taurine, carnosine, and anserine.

4. The method as claimed in claim 1, wherein the composition of the chicken liver hydrolysates increases the activity of alcohol dehydrogenase or aldehyde dehydrogenase.

5. The method as claimed in claim 1, wherein the composition of the chicken liver hydrolysates further decreases serum triglyceride and liver triglyceride induced after alcohol consumption.

6. The method as claimed in claim 1, wherein the composition of the chicken liver hydrolysates decreases collagen deposition and the gene expressions of collagen type 1α (Colα) and α-smooth muscle actin (α-SMA) in a liver.

7. The method as claimed in claim 1, wherein the composition of the chicken liver hydrolysates decreases the gene expressions of tumor necrosis factor-α (TNF-α), interleukin-6 (IL-6), and transforming growth factor-β (TGF-β).

8. The method as claimed in claim 1, wherein the composition of the chicken liver hydrolysates is orally administered to the individual in need thereof.

9. The method as claimed in claim 1, wherein the composition of the chicken liver hydrolysates is made as pills, capsules, tablets, granules, powders, oral solution or suspension.

* * * * *